United States Patent [19]

Thurman

[11] 4,315,928

[45] Feb. 16, 1982

[54] N-AMINOSULFENYL CARBAMATE COMPOUNDS, COMPOSITIONS AND USE

[75] Inventor: Duane E. Thurman, Salinas, Calif.

[73] Assignee: Union Carbide Corporation, New York, N.Y.

[21] Appl. No.: 590,463

[22] Filed: Jun. 26, 1975

[51] Int. Cl.$^3$ ............... C07C 161/00; C07D 295/22; A01N 41/12; A01N 43/84
[52] U.S. Cl. .................... 424/248.5; 424/298; 424/304; 544/159; 260/453.1; 260/464; 260/465 D; 260/465.4
[58] Field of Search ............... 260/247.1 R, 293.85, 260/327 P, 566 AC, 453 RW, 453.1, 464, 465.4, 465 D; 544/58, 97, 133, 145, 159, 383; 424/246, 248.5, 248.51, 250, 267, 277, 327, 298, 304

[56] References Cited

U.S. PATENT DOCUMENTS

| | | | |
|---|---|---|---|
| 3,843,689 | 10/1974 | Brown | 260/346.2 |
| 3,890,386 | 6/1975 | Kuhle et al. | 260/566 |
| 3,954,836 | 5/1976 | Siegle | 260/470 |

OTHER PUBLICATIONS

Fukuto et al, "Environmental Quality and Safety", supplement, vol. III, pp. 394–400, Jul., 1974.

*Primary Examiner*—John M. Ford
*Assistant Examiner*—R. W. Ramsuer
*Attorney, Agent, or Firm*—C. J. Vicari; R. C. Brown

[57] ABSTRACT

A novel class of N-aminosulfenyl carbamate compositions have outstanding insecticidal and miticidal properties coupled with very low toxicity to mammals and important economic crops.

39 Claims, No Drawings

N-AMINOSULFENYL CARBAMATE COMPOUNDS, COMPOSITIONS AND USE

This invention relates to novel compounds and their preparation and to novel methods and compositions for combating insects, and mites.

The compounds which are employed as the active ingredients in the pesticidal compositions of this invention are new compounds corresponding to the following general formula:

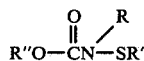

wherein:

R may be hydrogen, lower alkyl, lower cycloalkyl, lower alkenyl, lower alkoxy or lower cycloalkyl either unsubstituted or except where R is hydrogen, substituted with one or more chloro, bromo, fluoro, nitro or cyano substituents, or a combination thereof or phenyl or lower phenylalkyl, either unsubstituted or substituted with one or more chloro, bromo, fluoro, nitro, cyano, lower alkyl, lower haloalkyl or lower alkoxy substitutents or a combination thereof.

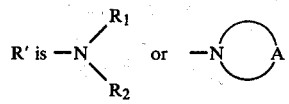

$R_1$ and $R_2$ are individually, hydrogen, alkyl, alkenyl, alkoxy, cycloalkyl, phenylalkyl or phenyl, all of which may be unsubstituted or substituted, except in the case of hydrogen, with one or more chloro, bromo, fluoro, nitro, cyano, lower alkyl, lower haloalkyl, or lower alkoxy substituents or a combination thereof; or a saturated or unsaturated five or six membered heterocyclic radical in which there are one or two hetero atoms which may be oxygen, sulfur in all of its oxidation states or nitrogen, including combinations thereof; all of which heterocyclic radicals may be unsubstituted or substituted with one or more chloro, bromo, fluoro, nitro, cyano, lower alkyl, lower haloalkyl, or lower alkoxy substituents or a combination thereof.

A is a divalent aliphatic chain which may be alkylene, alkenylene, or an aliphatic chain which may include one or two hetero atoms of oxygen, sulfur in all of its oxidation states or nitrogen or a combination thereof to form a five or six membered ring structure, which may be unsubstituted or substituted with one or more chloro, bromo, fluoro, nitro, cyano, lower alkyl, lower haloalkyl or lower alkoxy substituents or a combination thereof.

R" is an imino group of the formula:

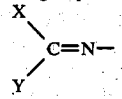

wherein X and Y are individually hydrogen, cyano, or chloro radicals or are alkyl, alkenyl, alkylthio, alkoxy, aryl, arylthio, carbamoyl, aminocarbonylalkyl or carbonylaminoalkyl groups or are joined together by a saturated or unsaturated divalent aliphatic chain which may be interupted by one or more sulfur in all of its oxidation states, oxygen or nitrogen atoms to form a five or six membered ring all of which may be substituted by one or more chloro, bromo, fluoro, nitro, cyano, lower alkyl, lower alkylthio, lower alkylsulfinyl, lower alkylsulfonyl or lower alkoxy substituents with the proviso that the total number of all aliphatic carbon atoms in R" should not exceed about 12 and should preferably be not more than 8.

It will be appreciated that when X and Y are different, the new compositions of this invention will exist in at least two isomeric forms. In the case where the oxygen atom of the oximino function is on the same side of the oximino double bond as is X, the conjugation is syn to X and anti to Y. When the oxygen atom is on the opposite side of the oximino double bond, the conjugation is anti to X and syn to Y. Both isomers exhibit biological activity, which is influenced by the character of the X and Y moieties. Both isomers are within the scope of this invention.

Preferred are those compounds in which R is lower alkyl, most preferably methyl, due to their generally greater pesticidal activity.

Novel compounds according to the generic formula above wherein R" is an imino group and X or Y is a lower alkyl thioalkyl moiety have exceptional pesticidal properties and are preferred compounds. Particularly preferred are compounds that have the generic structure:

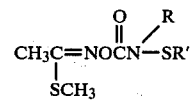

and R and R' are as defined above.

The new compositions of this invention can be prepared conveniently in accordance with the methods illustrated by the general reaction schemes set forth below in which the R, R' and R" are as defined above Method I:

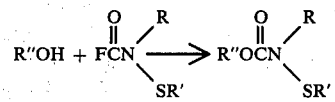

In Method I an appropriately substituted N-aminosulfenylcarbamoyl fluoride is allowed to react with an oxime in the presence of an acid acceptor. The reaction may be carried out in an inert solvent such as methylene chloride, chloroform, dioxane, tetrahydrofuran, benzene, toluene, acetone, dimethoxyethane, dimethylformaide, or acetonitrile. Acid acceptors which may be used include tertiary alkylamines such as triethylamine and trimethylamine and heterocyclic bases such as N-methylmorpholine, pyridine and quinoline or a metal salt of a phenol or oxime may be used. The temperature at which these reactions are carried out is not critical. Temperatures ranging from ambient to about 75° C. are normally used and preferred. Pressure is not critical in the conduct of these reactions. For convenience, the pressure used will normally be atmospheric or autogenous. Optionally, phase transfer catalysts such as crown catalyst may be used in the conduct of these reactions employing either heterogenous or homogeneous solvent systems.

The N-aminosulfenyl carbamoyl fluoride reactants employed in this reaction can be prepared conveniently by reacting an appropriately substituted carbamoyl fluoride compound with an appropriately substituted N-aminosulfenyl compound in the presence of an acid acceptor. The N-aminosulfenyl halide reactants are prepared by reacting a secondary amine compound with sulfur dichloride or by direct chlorination of bisaminodisulfides as described for example in British Pat. No. 790,021 and U.S. Pat. No. 3,400,125. The carbamoyl fluoride compounds are prepared by reacting an appropriately substituted isocyanate compound with hydrofluoric acid.

A preferred and novel route to the preparation of the N-aminosulfenyl halide reactant is by reacting an appropriately substituted secondary amine with $S_2Cl_2$ in the presence of an acid acceptor to form a bis-amine sulfenyl compound after which the desired N-aminosulfenyl halide compound is prepared by direct halogenation of the biscompound.

Method II

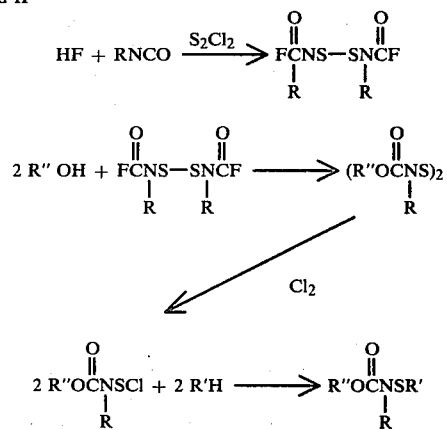

In Method II an N-substituted bis-(N-fluorocarbomyl)-amino-disulfide compound is prepared by reacting an appropriately substituted isocyanate compound with hydrogen fluoride in the presence of $S_2Cl_2$ and the resulting carbamoyl fluoride is then further reacted with an oxime compound to form the corresponding bis carbamate-N,N-disulfide compound, which upon halogenation, as with chlorine, yields an N-halosulfenyl carbamate which can then be reacted with an amine compound to yield the desired N-aminosulfenyl carbamate compound.

An alternative method of preparing the N-chlorosulfenyl reactant employed in the final step of Method II is by reacting an appropriately substituted carbamate having one hydrogen attached to the carbamoyl nitrogen (R″OCONHR) with $SCl_2$ in the presence of an acid acceptor to produce the desired product.

Method III:

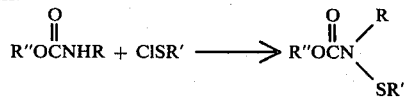

In Method III an appropriate carbamate composition is directly N-sulfenylated by reaction with an N-amino-N-sulfenyl halide, preferably a chloride. The reaction may be conducted in the presence of acid acceptor, if desired, although the use of such an acid acceptor is not a critical requirement.

Method IV:

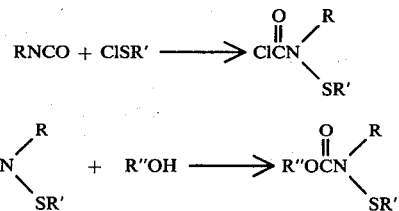

In this method an N-aminosulfenyl carbamoylchloride analagous to the carbamoyl chlorides of Method I is prepared by the direct addition of an appropriately substituted N-aminosulfenyl chloride to an appropriately substituted isocyanate compound. The resultant carbamoyl chloride is then allowed to react with the appropriate oxime compound in the presence of an acid acceptor, in an inert solvent to produce the desired N-aminosulfenyl substituted carbamate composition.

Method V:

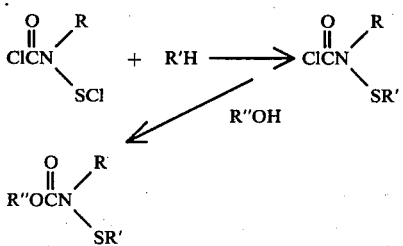

In method V a secondary amine compound is selectively sulfenylated with an appropriately substituted N-chlorosulfenyl carbamoyl chloride compound which may then be further reacted with a hydroxy compound such as an oxime or phenolic compound to yield the desired N-aminosulfenyl carbamate compound. The N-chlorosulfenyl carbamoyl chloride reactants employed in this method are known compounds and can be prepared for example by the method described in U.S. Pat. No. 3,699,163.

Product isolation in all of the above methods is preferably accomplished by the addition of cold water to the reaction mixture, when a water immiscible inert solvent has been employed, to remove the metal or amine salts. After several washings and dryings the solvent may be removed by evaporation to yield the crude product which can be used as such, recrystallized, or purified by chromatography. When the reaction is conducted with a water miscible solvent, the solvent is simply removed by evaporation, after filtration, if desired. Following solvent removal, cold water and a water immiscible solvent such as methylene chloride or chloroform are added to the residue and the mixture then processed as described above.

The following specific examples are provided to more particularly illustrate the manner in which the new compositions of this invention can be prepared.

EXAMPLE 1

Preparation of 4-Morpholinosulfenyl Chloride

A solution of 87.1 g (1.0 mole) morpholine in 100 ml of dry ether was slowly added over 2½ hours to 51.5 g (0.5 mole) of redistilled sulfur dichloride in 500 ml of dry ether at −10° C. under a nitrogen atmosphere. After the addition was completed the mixture was warmed to room temperature and filtered under nitrogen. The ether filtrate was very cloudy and was refiltered and then stripped in vacuo. Some solids remained so the residue was again filtered into a distillation flask and vacuum distilled to give 27 g of 4-morpholinosulfenyl chloride, b.p. 62° C./0.75 mm (35% yield).

EXAMPLE 2

Preparation of N-Methyl-N-(4-Morpholinosulfenyl)carbamoyl Fluoride

Anhydrous hydrogen fluoride (3.4 g, 0.17 mole) was added to 200 ml of toluene at −10° C. in a polyethylene reactor equipped with a stainless steel stirrer and thermocouple well, and a polyethylene dry ice condenser. Methylisocyanate (9.35 g, 0.17 mole) was then added dropwise; the temperature was maintained at −10° C. or less. Then, 26.3 g (0.17 mole) of freshly distilled 4-morpholinosulfenyl chloride was added to the mixture over a 20 minute period, and finally, 17.3 g (0.17 mole) triethylamine was added at −10° C. After the addition was completed the mixture was stirred and allowed to warm to room temperature for 30 minutes. It was filtered and the toluene filtrate was extracted twice with water and dried with magnesium sulfate. The toluene was removed in vacuo, and the residue was dissolved in boiling hexane, treated with Darco, filtered, and chilled. The resulting crystals were collected by suction filtration, and dried in vacuo to give 20 g, of N-methyl-N-(4-morpholinosulfenyl)carbamoyl fluoride, m.p. 48°-50° C. (60.5 percent yield).

EXAMPLE 3

Preparation of S-Methyl N-[N'-Methyl-N'-(4-Morpholinosulfenyl)carbamoyloxy]-thioacetimidate Triethylamine (5.1 g, 0.05 mole) was added dropwise to a stirred mixture of 9.71 g (0.05 mole) of N-methyl-N-(4-morpholinosulfenyl)carbamoyl fluoride and 5.25 g (0.05 mole) of S-methyl-N-hydroxythiolactimidate in 75 ml of tetrahydrofuran at 0° C. The solution was then stirred at room temperature for 24 hrs. No amine salt solids were visible so the solution was concentrated in vacuo, and the residue was taken up in chloroform and was extracted with water and saturated sodium bicarbonate solution. The chloroform solution was dried with magnesium sulfate, was concentrated in vacuo, and the resulting solids were recrystallized from benzene/hexane to give 10 g (71.6 percent yield) of S-Methyl N-[N'-Methyl-N'-(4-Morpholinosulfenyl)carbamoyloxy]-thioacetimidate, m.p. 125°-127° C.

Infrared: 5.8μ, C=O; 6.34μ, C=N; 7.04μ, NCH$_3$; 14.45μ, C—S.

NMR: CDCl$_3$; singlet at δ2.26 ppm, 3H, CH$_3$C=; singlet at δ2.34 ppm, 3H, CH$_3$S—δ; singlet at δ3.39 ppm, 3H, >N-CH$_3$; multiplets, 4H each, at δ3.28 and 3.63 ppm, morpholine ring.

Anal. Calc'd. for C$_9$H$_{17}$N$_3$O$_3$S$_2$: C, 38.69; H, 6.13; N, 15.04. Found: C, 38.77; H, 5.88; N, 14.92.

EXAMPLE 4

Preparation of S-Ethyl-N-[N'-Methyl-N'-(4-Morpholinosulfenyl)Carbamoyloxy]Thioacetimidate Triethylamine (5.1 g, 0.05 mole) was added over one-hour at 25° C. to a solution of 6.0 g (0.05 mole) S-ethyl N-hydroxy thioacetimidate and 9.7 g (0.05 mole) of N-methyl-N-(4-morpholinosulfenyl)carbamoyl fluoride in 150 ml of benzene. The mixture was stirred at 40° C. for 4 hours, and then stirred at room temperature overnight. The benzene solution was water-washed three times, dried with magnesium sulfate, and the solvent was evaporated in vacuo. The oily residue was triturated with n-hexane, and the solids thus liberated were collected by filtration and were recrystallized from diisopropyl ether to give 5 g (34 percent yield) of S-ethyl-N-[N'-methyl-N'-(4-morpholinosulfenyl)carbamoyloxy]thioacetimidate, m.p. 80°-82° C.

Anal. Calc'd for C$_{10}$H$_{19}$N$_3$O$_3$S$_2$: C, 40.9; H, 6.5, N, 14.3. Found: C, 41.2; H, 6.3, N, 14.4.

EXAMPLE 5

Preparation of 2-N-[N'-Methyl-N'-(4-Morpholinosulfenyl)Carbamoyloxy]imino-1,4-Dithiane A mixture of 7.3 g (0.05 mole) of 2-oximino-1,4-dithiane, 9.7 g (0.05 mole) of N-methyl-N-(4-morpholinosulfenyl)carbamoyl fluoride, and 5.1 g of triethylamine in 200 ml of 1,4-dioxane was stirred at 60° C. for 10 hrs. and then at 75° C. for 4 hrs. Then the dioxane was removed in vacuo. The residue was taken up in methylene chloride and was extracted twice with water. The methylene chloride solution was dried with anhydrous magnesium sulfate and was concentrated in vacuo. Diethyl ether was added to the solid residue and the mixture was filtered. The precipitated solids were then recrystallized from ethyl acetate to give 10 g. (62.1 percent yield) of 2-N-[N'-Methyl-N'-(4-morpholinosulfenyl)carbamoyloxy]imino-1,4-dithiane, m.p. 152°-154° C.

Anal. Calc'd. for C$_{10}$H$_{17}$N$_3$O$_3$S$_3$: C, 37.1; H, 5.3; N, 13.0. C, 36.9; H, 5.0; N, 12.9.

EXAMPLE 6

Preparation of 2-Methyl-2-(Methylthio)propionaldehyde O-[N-Methyl-N-(4-Morpholinosulfenyl)Carbamoyl]oxime A solution of 6.7 g (0.05 mole) of 2-methyl-2-(methylthio)propionaldoxime, 5.1 g of triethylamine, and 9.7 g (0.05 mole) of N-methyl-N-(4-morpholinosulfenyl)carbamoyl fluoride in 150 ml of benzene was stirred 48 hrs. at 60° C. After cooling, the mixture was extracted with water and with a saturated sodium bicarbonate solution. After drying, the benzene solvent was removed under vacuum. The resultant oil was added to 300 ml of n-hexane and was allowed to set for 3 days during which time solids precipitated. The mixture was filtered, and the solids were recrystallized from isopropanol to give 2.2 g (14.3 percent yield) of 2-methyl-2-(methylthio)propionaldehyde O-[N-methyl-N(4-morpholinosulfenyl)carbamoyl]oxime, m.p. 71°-73° C.

Infrared: 5.79, C=O; 6.2μ, C=N; 9.25μ, NOC; 10.63μ, =N—O.

NMR: CDCl$_3$; singlet at δ1.49 ppm (6H); singlet at δ2.00 ppm (3H); singlet at δ3.40 ppm (3H); multiplets (4H each) at δ3.28 and δ3.64 ppm.

Anal. Calc'd for C$_{11}$H$_{21}$N$_3$O$_3$S$_2$: C, 43.0; H, 6.9; N, 13.7. C, 43.1; H, 6.6; N, 13.6.

EXAMPLE 7

Preparation of S-Isopropyl N-[N'-Methyl-N'-(4-Morpholinosulfenyl)carbamoyloxy]thioacetimidate A solution of 8.7 g of N-methyl-N-(4-morpholinosulfenyl)carbamoyl fluoride, 5.32 g (0.04 mole) of S-isopropyl N-hydroxythioacetimidate, and 4.1 g of triethylamine in 75 ml of benzene was heated 3 hours at 55° C., stirred 18 hours at room temperature, and then heated 6 hr. at 75° C. After cooling, the solution was extracted twice in water and once with aqueous sodium bicarbonate solution. The solution was then dried (MgSO$_4$), concentrated under vacuum, and the solid residue was recrystallized from diisopropyl ether to give 6 g (49 percent yield) of S-isopropyl N-[N'-methyl-N'-(4-morpholinosulfenyl)carbamoyloxy]thioacetimidate, m.p. 89°–91° C.

Infrared: 5.78μ, C=O; 6.33μ, C=N; 10.65μ, =N—O.

NMR: CDCl$_3$; doublet at δ 1.37 ppm (6HO, J=6.5 Hz; singlet at δ 2.36 ppm, (3H); and a singlet at δ 3.42 super imposed on multiplets at δ 3.30 and δ 3.64 ppm (total 12H).

Anal. Calc'd. for C$_{11}$H$_{21}$N$_3$O$_3$S$_2$; C, 42.97; H, 6.88; N, 13.67. Found: C, 42.88; H, 6.66; N, 13.62.

EXAMPLE 8

Preparation of S-(2-Cyanoethyl)-N-[N'-Methyl-N'-(4-Morpholinosulfenyl)carbamoyloxy]thioacetimidate Triethylamine (5.1 g) was added to a stirred solution of 9.71 g (0.05 mole) of N-methyl-N-(4-morpholinosulfenyl)carbamoyl fluoride and 7.21 g (0.05 mole) of S-(2-cyanoethyl) N-hydroxythioacetimidate in 75 ml of tetrahydrofuran at 25° C. The mixture was stirred for 20 hrs., and then was filtered. The solids were washed with tetrahydrofuran and then hexane. After vacuum drying, 1 g of white product was obtained, m.p. 122°–123° C.

The tetrahydrofuran filtrate was concentrated under vacuum, and the resultant residue was taken up in chloroform. The chloroform solution was then washed with water, 10% potassium carbonate, and water again, dried (MgSO$_4$), filtered, and stripped in vacuo. The residue was recrystallized from tetrahydrofuran/hexane to give 10.1 g of S-(2-cyanoethyl)-N-[N'-methyl-N'-(4-morpholinosulfenyl)carbamoyloxy]thioacetimidate, m.p. 122° C. (70% overall yield).

Infrared: 4.45μ, C≡N; 5.8μ, C=O; 6.23μ, C=N.

NMR: Acetone d$_6$; singlet at α 2.38 ppm (3H) for CH$_3$C, =N—; a singlet at α 3.42 ppm (—NCCH$_3$)S—.

Anal. Calc'd for C$_{11}$H$_{18}$N$_4$O$_3$S$_2$: C, 41.49; H, 5.70, N, 17.96. Found: C, 41.20; H, 5.61, N, 17.34.

EXAMPLE 9

Preparation of 5-Methyl-4-N-[N'-Methyl-N'-(4-Morpholinosulfenyl)-carbamoyloxy]imino-1,3-Oxathiolane A mixture of 7.36 g (0.05 mole) of 5-methyl-4-hydroximino-1,3-oxathiolane, 9.71 g (0.05 mole) of N-methyl-N-(4-morpholinosulfenyl)carbamoyl fluoride, and 5.1 g of triethylamine was stirred at room temperature for 24 hours. The mixture was concentrated under vacuum, and the residue was taken up in methylene chloride and solution was washed two times with water, dried (MgSO$_4$), and was concentrated in vacuo. A brown syrup was obtained which was purified by column chromatography on silica gel using 90/10 methylene chloride/hexane, methylene chloride, and 3/1 methylene chloride/acetonitrile stepwise gradient elution. A yield of 3.5 g (23% yield) of a viscous syrup was obtained which was pure by thin layer analysis, ir, nmr, and elemental analyses. Upon standing the syrup slowly solidified, to yield the desired product, 5-methyl-4-N-[N'-methyl-N'-(4-morpholinosulfenyl)carbamoyloxy]imino-1,3-oxathiolane, m.p. 73°–75° C.

Anal. Calc'd for C$_{10}$H$_{17}$N$_3$O$_4$S$_2$: C, 39.07; H, 5.58; N, 13.67. Found: C, 39.07; H, 5.53; N, 13.52.

EXAMPLE 10

Preparation of 2-Cyano-2-Methylpropionaldehyde O-[N-Methyl-N-(4-Morpholinosulfenyl)Carbamoyl]oxime Using the procedure of Example 9, 2-cyano-2-methylpropionaldehyde O-[N-methyl-N-(4-morpholinosulfenyl)carbamoyl]oxime was obtained as a viscous syrup (17.5 percent yield) after column chromatographic purification. This product would not crystallize.

Infrared: 4.46μ, C≡N; 5.77μ, C=O; 6.1μ, C=N; 10.6μ, =N—O.

NMR: CDCl$_3$; singlet at δ 1.65 ppm (6H); singlet at δ 3.42 ppm (3H); multiplets at δ 3.28 and 3.69 ppm (4H each), singlet at δ 7.78 ppm. (1H).

EXAMPLE 11

Preparation of S-Methyl N-[N'-Methyl-N'-(Dimethylaminosulfenyl)carbamoyloxy]thioacetimidate A mixture of 5.25 g (0.05 mole) of S-methyl-N-hydroxythioacetimidate, 7.9 g of N-methyl-N-(dimethylaminosulfenyl)carbamoyl fluoride, and 5.1 g of triethylamine in 75 ml of tetrahydrofuran was stirred and heated at 40°–60° C. for 3 hrs. and then at 25° C. for 8 hrs. The solvent was removed in vacuo, and the residue was taken up in chloroform. This solution was extracted with water and 10% potassium carbonate, dried (MgSO$_4$) and then was concentrated in vacuo. The crude syrupy residue obtained was purified by column chromatography on silica gel to give 1.6 g of S-methyl N-[N'-methyl-N'-(dimethylaminosulfenyl)-carbamoyloxy]thioacetimidate, a yellow syrup.

Infrared: 3.55μ, N(CH$_3$)$_2$; 5.8μ, C=O; 6.3μ, C=N.

NMR: CDCl$_3$; singlet at δ 2.28 ppm (3H); singlet at α2.41 ppm. (3H); singlet at α 2.97 ppm (6H); singlet at α 3.43 ppm (3H).

Anal. Calc'd for C$_7$H$_{15}$N$_3$O$_2$S$_2$: C, 35.42; H, 6.37; N, 17.70. Found: C, 35.06; H, 6.02; N, 16.98.

EXAMPLE 12

Preparation of S-Methyl-N-[N'-Methyl-N'-(1-Piperidinosulfenyl)Carbamoyloxy]Thioacetimidate Sodium hydride (1.44 g, 0.06 mole, mineral oil free) was added by increments under nitrogen atmosphere into a solution of 6.30 g (0.06 mole) of S-methylN-hydroxythioacetimidate in 100 ml of toluene at 0°–2° C. The resulting slurry was stirred for 0.75 hr. and allowed to warm to room temperature. To this mixture was added a solution of 8.6 g (0.045 mole) of N-methyl-N-(1-piperidinosulfenyl) carbamoyl fluoride in 10 ml of toluene over 35 min. at 18°-23° C. At the completion of the addition, the reaction mixture turned to a clear light yellow solution. After stirring for an additional 0.5 hr., 100 ml of water was added slowly. The organic phase was washed with water, dried over anhydrous magnesium sulfate, filtered, and concentrated. The resulting brown oil (6.0 g) was recrystallized from diisopropyl ether/hexane to give 2.2 g (18%) of S-methyl-N-[N'-methyl-N'-(1-piperidinosulfenyl)carbamoyloxy]thioacetimidate, m.p. 65°-66° C.

Infrared: 3.5μ (N-CH$_2$); 5.8μ (C=O); 6.3μ (C=N); 7.07μ (N-CH$_3$); 9.3μ (N-O-C); 12.85μ

(—NOCN—)

NMR(CDCl$_3$): δ 1.50 (m, 6H, —CH$_2$—, β and γ to N); δ 2.29 (s, 3H, CH$_3$—C=N); δ 2.41 (S, 3H, CH$_3$—S—); δ 3.29 (m, 4H, —CH$_2$— γ to N); δ 3.41 (S, 3H, CH$_3$—N—CO).

Anal. Calculated for C$_{10}$H$_{19}$N$_3$O$_2$S$_2$: C, 43.30; H, 6.90; N, 15.15. Found: C, 42.80; H, 6.71; N, 14.99.

EXAMPLE 13

Preparation of N-Isopropyl-N'(4-Morpholinosulfenyl)Carbamoyl Fluoride

To a mixture of 8.0 g (0.4 mole) of anhydrous hydrogen fluoride and 200 ml of methylene chloride in a polyethylene reactor fitted with a stainless steel stirrer and a thermocouple well was added 34.1 g (0.4 mole) of isopropyl isocyanate over a 0.5 hr. period at 0° C. The mixture was stirred for 1.5 hr at 0.2° C., and then 4-morpholinosulfenyl chloride, prepared in situ by evaporating 14.5 g (0.2 mole) of chlorine into a slurry of 47.3 g (0.2 mole) of 4,4'-dithiobismorpholine in 100 ml of methylene chloride at −10° C., followed by stirring the mixture for 0.5 hr. at −10° C. to 0° C., and then sparging it with nitrogen for 0.5 hr. Triethylamine (40.4 g, 0.4 mole) was added over a 45 minute period at −10° C. The mixture was stirred for one hour and allowed to warm to room temperature in 1 hr. Water (200 ml) was added slowly while the mixture was stirred vigorously. The organic phase was washed with water, dried with anhydrous magnesium sulfate, filtered, and concentrated to give 53.0 g yellow il, which upon recrystallization from hexane (chilled with dry-ice), yielded 24 g (27%) of product, m.p. 46°-48° C. and 1.6 g of N-(N'-isopropylcarbamoyl)-morpholine as a by-product. The desired product N-isopropyl-N'(4-morpholinosulfenyl)-carbamoyl fluoride, crystallized out last.

Infrared: 5.65μ (C=O); 7.23 and 7.35μ (CHMe$_2$); 7.85μ (C—F); 9.0μ (C—O—C).

NMR (CDCl$_3$): δ 1.25 and δ 1.37 (two doublets, J=1.5 Hz, 6H, —CHMe$_2$); δ 3.25 and δ 3.72 (two multiplets, 8H, morpholine ring protons); δ 4.14 (m, J=7 Hz, 1H, CHMe$_2$).

Anal.: Calculated for C$_8$H$_{15}$FN$_2$O$_2$S: C, 43.23; H, 6.80; N, 12.60. Found: C, 43.41; H, 6.72; N, 12.69.

By-product, (N-[N'-isopropylcarbamoyl]morpholine):

Infrared: 2.96μ (NH); 6.15μ (C=O); 6.45μ (CNH); 9.0μ (C—O—C).

NMR(CDCl$_3$): δ 1.15 (d, J=7 Hz, 6H, CHMe$_2$); δ 3.30 and δ 3.72 (m, 8H, morpholine ring protons); δ 3.88 to δ 4.60 (m, 2H, one of which exchanged with D$_2$O).

Anal.: Calculated for C$_8$H$_{16}$N$_2$O$_2$: C, 55.79; H, 9.37; N, 16.26. Found: C, 55.56; H, 9.40; N, 16.22.

EXAMPLE 14

Preparation of S-Methyl-N-[N'-Isopropyl-N'-(4-Morpholinosulfenyl)-Carbamoyloxy]Thioacetimidate To a mixture of 1.68 g (0.67 mole) of mineral oil free sodium hydride and 100 ml of toluene was added under a nitrogen atmosphere a solution of 7.35 g (0.07 m) S-methyl N-hydroxy thioacetimidate in 50 ml of toluene over a 1.5 hr. period at 0.5° C. The mixture was allowed to warm to room temperature for one hour. N-Isopropyl-N'(4-morpholinosulfenyl)carbamoyl fluoride (15.4 g, 0.07 mole) in 25 ml of toluene was added dropwise at 23°-27° C. over a 35 min period. After one hour of stirring, 100 ml of water was added. The toluene layer was washed with water, dried with anhydrous magnesium sulfate, filtered, and concentrated to give 20 g yellow oil which solidified on standing, Recrystallization of the solid from diisopropyl ether yielded 9.9 g (46%) of S-methyl-N-[N'-isopropyl-N'-(4-morpholinosulfenyl)carbamoyloxy]thioacetimidate, m.p. 83°-84° C.

Infrared: 5.8μ (C=O); 6.3μ (C=N).

NMR(CDCl$_3$)=δ1.32 (d, J=7H$_2$, 3H, CHMe$_2$); δ 2.32 (S, 3H, CH$_3$—C=); δ 2.42 (S, 3H, CH$_3$—S—C=); δ 3.24 and δ 3.67 (two multiplets, 8H, morpholine ring protons); δ 4.26 (m, J=7 Hz, 1H, CHMe$_2$).

EXAMPLE 15

Preparation of N-Methyl-N(1-Piperidinosulfenyl)Carbamoyl Fluoride

Anhydrous hydrogen fluoride (10.0 g, 0.5 mole) was added to 400 ml of methylene chloride at −10° C. in a polyethylene reactor fitted with a stainless steel stirrer and a thermocouple well. To this solution was added 28.6 g (0.5 mole) of methyl isocyanate in 15 min. at −10° C. The mixture was stirred for 20 min. To the mixture was then added 1-piperidinosulfenyl chloride, prepared in situ by evaporating 18.0 g (0.25 mole) of chlorine into a slurry of 58.1 g (0.25 mole) of 1,1'-dithiobispiperidine in 150 ml of methylene chloride at −10° C., followed by stirring the mixture for 0.5 hr. and then sparging it with nitrogen for 20 min. to remove the excess chlorine. Triethylamine (50.6 g, 0.5 mole) was added dropwise to the above mixture at −10° C. The mixture was stirred for 0.5 hr. and then allowed to warm to 0° C. After the addition of 250 ml of water, the methylene chloride layer was agitated thoroughly and was washed once again with 250 ml of water, dried over anhydrous magnesium sulfate, filtered and concentrated to give 61 g reddish liquid residue. Distillation of the residue at 74°-76° C./0.38 mm yielded 44.2 g of N-methyl-N-(1-piperidinosulfenyl)carbamoyl fluoride, (46%) as an amber liquid.

Infrared: 3.5μ (N—CH$_2$); 5.6μ (C=O); 7.05μ (N-CH$_3$); 7.78μ (C—F).

NMR (CDCl$_3$): δ 1.52 (m, 6H, —CH$_2$— β and γ to N); δ 3.28 (m, 4H, —CH$_2$— γ to N); δ 3.35 (δ, J=1 Hz, 3H, N—CH$_3$).

Anal. Calculated for C$_7$H$_{13}$FN$_2$OS: C, 43.73; H, 6.81; N, 14.57. Found: C, 43.57; H, 6.50; N, 14.44.

EXAMPLE 16

Preparation of
3,3-Dimethyl-2-N-[N'-Methyl-N'-(4-Morpholinosulfenyl)Carbamoyloxy]imino-5-Oxo-Perhydro-1,4-Thiazine A mixture of 3.0 g (0.017 mole) of 3,3-dimethyl-2-oximinoperhydro-1,4-thiazin-5-one, 3.3 g (0.017 mole) of N-methyl-N-(4-morpholinosulfenyl)carbamoyl fluoride, and 1.7 g of triethylamine in 200 ml of benzene was stirred at 70° C. for 4 hours. After cooling and filtering, the benzene solution was washed with water, dried (MgSO$_4$), and concentrated. The residue was recrystallized from acetonitrile to give 2 g (34 percent yield) of 3,3-dimethyl-2-N-[N'-methyl-N'-(4-morpholinosulfenyl)carbamoyloxy]imino-5-oxo-perhydro-1,4-thiazine, m.p. 180°-2° C.

Anal. Calc'd. for $C_{12}H_{20}N_4O_4S_2$: C, 41.4; H, 5.8; N, 16.1. Found: C, 41.2; H, 6.1; N, 15.8.

EXAMPLE 17

Preparation of
S-Methyl-N-[N'-Methyl-N'-Diethylaminosulfenyl)Carbamoyloxy]Thioacetimidate Sodium hydride (1.8 g, 0.078, mineral oil free) was stirred at 0° C. in 75 ml of toluene. To this was added, dropwise, a solution of 8.2 g. (0.078 mole) of S-methyl-N-hydroxythioacetimidate in 75 ml of toluene. The mixture was stirred and warmed to room temperature. When the hydrogen evolution ceased, a toluene (25 ml) solution of 14.0 g (0.078 mole) of N-methyl-N-(diethylaminosulfenyl)carbamoyl fluoride was added to the mixture. After stirring 1 hr. at room temperature, the mixture was extracted with water (100 ml) four times, dried (MgSO$_4$), and concentrated. A heavy syrup was obtained which would not crystallize and which was shown by thin layer chromatography to contain starting materials. This syrup was purified by column chromatography on silica gel and subsequent recrystallization from cyclohexane afforded 2.7 g of S-methyl-N-N'-methyl-N'(diethylamino-sulfenyl)carbamoyloxy thioacetimidate, (13 percent yield), m.p. 47.5°-49.5° C.

Anal. Calc'd for $C_9H_{19}N_3O_2S_2$: C, 40.73; H, 7.2; N, 15.83. Found: C, 40.68; H, 7.05; N, 15.87.

EXAMPLE 18

Preparation of
N-Methyl-N-(Dimethylaminosulfenyl)carbamoyl Fluoride

Anhydrous hydrogen fluoride (14.2 g., 0.71 mole) was added to 400 ml toluene at −50° C. and this solution was then charged to a polyethylene reactor. Methyl isocyanate (41.0 g, 0.71 mole) was then added dropwise over a 15-minute period. The mixture was stirred and warmed to 0° C. for 1 hr. N,N-Dimethylaminosulfenyl chloride (80.0 g, 0.71 mole, freshly distilled) was then added dropwise over a 5 minute period. The reaction mixture was allowed to warm to 10° C., and then 74 g of triethylamine was added dropwise. External cooling was used to maintain the temperature at 5°-10° C. After the addition was completed the mixture was stirred at ambient temperature for 1 hr., filtered, and the organic filtrate was water washed. The toluene solution was dried (MgSO$_4$), concentrated in vacuo, and the residue was vacuum distilled to give 55 g of N-methyl-N-(dimethylaminosulfenyl)carbamoyl fluoride, b.p. 55°-57° C./5.0 mm (50.9 percent yield).

EXAMPLE 19

Preparation of
N-Methyl-N-(4-Morpholinosulfenyl)carbamoyl Fluoride

This example illustrates a variation of the method described in Example 2, in which 4-morpholinosulfenyl chloride is prepared and used in situ.

Sulfur monochloride (135.1 g, 1.0 mole) was added dropwise at −15° C. to a solution of 174.2 g (2.0 mole) of morpholine and 202.4 g (2.0 mole) of triethylamine in 1700 ml of dry methylene chloride. External cooling was used to hold the reaction temperature at −15° C. during the addition. The mixture was stirred 0.5 hr. at −15° C. and then was warmed to room temperature and was extracted twice with water (500 ml). The organic solution of 4,4'-bismorpholine disulfide was then dried (MgSO$_4$), filtered, charged to a 3 liter reactor, and was cooled to −15° C. for chlorination.

Chlorine (71 g, 1 mole) was evaporated from a tared cold trap into the stirred solution of 4,4'-bis-morpholine disulfide. The temperature was maintained at −10° to −15° C. during the addition. After the addition was completed, a nitrogen sparge was used to expel any excess chlorine. The resulting solution of 4-morpholinosulfenyl chloride was then used immediately in a reaction with methylcarbamoyl fluoride, prepared via: Anhydrous hydrogen fluoride (40 g) was added to 500 ml of methylene chloride at −10° C. in a polyethylene reactor. Methylisocyanate (114 g) was then added slowly at −10° C. The mixture was stirred for 1 hr. at 0° C., and then recooled to −10° C. The methylene chloride solution of 4-morpholinosulfenyl chloride, prepared as described above, was then added rapidly. The mixture was stirred at 0° C. for 0.5 hr., and then 202 g of triethylamine was added dropwise. This mixture was stirred at 0° C. for 0.5 hr., and then was extracted three times with water, dried (MgSO$_4$), and concentrated in vacuo. The residue was dissolved in boiling benzene, treated with decolorizing charcoal, gravity filtered, and concentrated. Recrystallization from hexane, then afforded 186 g of N-methyl-N-(4-morpholinosulfenyl)carbamoyl fluoride, (46.7 percent yield based on morpholine).

EXAMPLE 20

Preparation of
S-Methyl-N-[N'-Methyl-N'-(4-morpholinosulfenyl)-Carbamoyloxy]Thioacetimidate This example describes a variation of the method employed in Example 3 in which a drawn ether is used to catalyze the reaction.

Powdered potassium hydroxide was slurried under nitrogen with 800 ml of benzene. Then S-methyl-N-hydroxythioacetimidate (39.3 g) and 0.2 g of dicyclohexyl-18-crown-6 were added, and the mixture was stirred 1 hour at room temperature. Then 73.8 g of N-methyl-N-(4-morpholinosulfenyl)carbamoyl fluoride was added portionwise. The mixture was stirred 2 hrs. at room temperature and extracted with 500 ml of water. Some solid product precipitated during this operation; these were collected by filtration and held for recrystallization. The benzene filtrate was basic (to pH 8). Therefore, it was neutralized with dilute HCl to pH 6, dried (MgSO$_4$), and concentrated. The resulting residue and the solids from above were combined and recrystallized from zylene/hexane to give 91 g (86.9 percent yield) of S-methyl-N-[N'-methyl-N'-(4-morpholinosulfenyl)carbamoyloxy]thioacetimidate.

EXAMPLE 21

Preparation of S-Methyl N-[N'-Methyl-N'-(Dimethylaminosulfenyl)carbamoyloxy]thioacetimidate This example describes a variation of the method employed in Example 11.

A mixture of 7.4 g (0.07 mole) of S-methyl N-hydroxythioacetimidate, 10.6 g S-methyl-N-(dimethylaminosulfenyl)carbamoyl fluoride, and 7.1 g triethylamine in 200 ml of benzene was heated at 78° C. for 6 hrs. The solution was cooled and extracted four times with water, dried (MgSO$_4$), and stripped in vacuo. The oily residue which solidified upon standing was recrystallized from diisopropyl ether to give 2 g (12 percent yield) of S-methyl N-methyl N-[N'-methyl-N'-(dimethylaminosulfenyl)carbamoyloxy]thioacetimidate, m.p. 66°–68° C.

EXAMPLE 22

Preparation of S-Methyl N-[N'-Methyl-N'-(Dimethylaminosulfenyl)Carbamoyloxy]Thioacetimidate This example illustrates still another process variation from the methods employed in Examples 11 and 21 to produce the title compound.

Powdered potassium hydroxide (3.3 g), 5.2 g of S-methyl-N-hydroxythioacetimidate, 0.1 g dicyclohexyl-18-crown-6, and 200 ml of benzene were stirred at room temperature for 0.5 hr. Then 8.0 g of N-methyl-N-(dimethylaminosulfenyl)carbamoyl fluoride was added slowly at 28° C. The reaction temperature was held at 28°–32° C. with external cooling. The mixture was stirred for 1 hr., and then was washed with water until neutral. After drying (MgSO$_4$), the solution was concentrated in vacuo, and the residue was recrystallized from diisopropyl ether to give 9.0 g (76 percent yield) of S-methyl N-[N'-methyl-N'-(dimethylaminosulfenyl)-carbamoyloxy]Thioacetimidate, m.p. 68°–70° C.

EXAMPLE 23

Preparation of 2-N-[N'-Methyl-N'-(Dimethylaminosulfenyl)carbamoyloxy]imino-1,4-Dithiane Dioxane (200 ml), powdered potassium hydroxide (3.3 g), dicyclohexyl-18-crown-6 (0.1 g), and 2-oximino-1,4-dithiane 7.5 g (0.05 mole) were combined and stirred at room temperature for 0.5 hr. Then 8.0 g N-methyl-N-(dimethylaminosulfenyl)-carbamoyl fluoride was added over a 2 minute period. The reaction mixture was stirred at 28°–32° C. for 2 hrs. The dioxane solution was then poured into 1000 ml of cold water and stirred. The aqueous mixture was extracted with methylene chloride, and the methylene chloride solution was back extracted with water, dried (MgSO$_4$), and stripped in vacuo. The product residue was recrystallized from 2-propanol to give 11 g (78.2 percent yield) of 2-N-N'-methyl-N'-(dimethylaminosulfenyl)carbamoyloxy imino-1,4-dithiane, m.p. 102°–104° C.

Anal. Calc'd. for C$_8$H$_{15}$N$_3$O$_2$S$_3$: C, 34.1; H, 5.4; N, 14.9. Found: C, 34.0; H, 5.3; N, 14.8.

EXAMPLE 24

Preparation of S-Isopropyl-N-[N'-Methyl-N'-(Dimethylaminosulfenyl)carbamoloxy]thioacetimidate N-Methyl-N-(dimethylaminosulfenyl)carbamoyl fluoride (8.0 g., 0.05 mole) was added at 28° C. to a stirred mixture of 6.7 g (0.05 mole) of 1-(2-propylthio)acetaldoxime, 3.3 g powdered potassium hydroxide, and 0.1 g of dicyclohexyl-18-crown-6 in 200 ml of benzene. The mixture was stirred at room temperature for 2 hours, extracted three times with water, dried (MgSO$_4$), and concentrated in vacuo. The residue was recrystallized from n-hexane to give 10 g (75.5 percent yield) of S-isopropyl-N-[N'-methyl-N'-(dimethylaminosulfenyl)carbamoyloxy]thioacetimidate, m.p. 55°–57° C.

Anal. Calc'd. for C$_9$H$_{19}$N$_3$O$_2$S$_2$: C, 40.7; H, 7.2; N, 15.8. Found: C, 41.0 H, 7.2 N, 15.8.

EXAMPLE 25

Preparation of N-Methyl-N-(Diethylaminosulfenyl)carbamoyl Fluoride

Anhydrous hydrogen fluoride (3.0 g, 0.15 mole) was added to 150 ml of methylene chloride at −10° C. Then 8.6 g of methylisocyanate was added, followed by 20.9 g (0.15 mole) of N,N-diethylaminosulfenyl chloride at 0° C. Triethylamine (15.2 g) was then added at 0° C. over a 15-minute period, and the mixture was stirred at +5° C. for 1 hour. The mixture was then extracted with water (100 ml), saturated sodium bicarbonate solution, and water again. After drying (MgSO$_4$), the solvent was removed in vacuo, and the crude residue was vacuum distilled to give 17 g of N-methyl-N-(diethylaminosulfenyl)carbamoyl fluoride, b.p. 57° C./0.8 mm (62.9 percent yield).

Anal. Calc'd. for C$_6$H$_{13}$FN$_2$O$_5$: C, 39.98; H, 7.27; N, 15.54. Found: C, 39.82; H, 6.83; N, 14.95.

EXAMPLE 26

Preparation of N-Phenyl-N-(4-Morpholinesulfenyl)carbamoyl Fluoride

Anhydrous hydrogen fluoride (4.0 g) was added to methylene chloride (150 ml) at −10° C. in a polyethylene reactor. Phenyl isocyanate (23.8 g, 0.2 mole) was then added dropwise over a 20 minute period. This mixture was stirred at 5° C. for 1 hour, and then a solution of 30.6 g (0.2 mole) of 4-morpholinosulfenyl chloride in 75 ml of methylene chloride was added rapidly. Triethylamine (20.2 g) was then added slowly at −10° C. The mixture was then stirred and warmed to 0° C. for 1 hr., water extracted twice, dried (MgSO$_4$), and concentrated in vacuo. The resulting dark residue was vacuum distilled to remove volatile impurities, and then the kettle residue was extracted with hot hexane. The hexane solution upon cooling deposited 6 g of N-phenyl-N-(4-morpholinesulfenyl)carbamoyl fluoride, m.p. 71°–72° C., (11 percent yield).

Infrared: 5.6$\mu$, C=O.

NMR: CDCl$_3$; multiplets at δ 3.25 and 3.66 ppm (4H each); singlet at δ 7.36 ppm (5H).

Anal. Calc'd. for C$_{11}$H$_{13}$FN$_2$O$_2$S: C, 51.55; H, 5.11; N, 10.93 Found: C, 52.27; H, 5.41; N, 10.94.

EXAMPLE 27

Preparation of
N-Methyl-N-(Di-n-butylaminosulfenyl)carbamoyl
Fluoride

Anhydrous hydrogen fluoride (2.14 g, 0.107 mole) was added to 125 ml of methylene chloride at $-10°$ C. Methyl isocyanate (6.12 g, 0.107 mole) was then added dropwise. The mixture was stirred 1 hour at 5° C., and then was cooled to $-10°$ C. again. Di-n-butylaminosulfenyl chloride (21.0 g, 0.107 mole, freshly distilled, b.p. 72° C./0.35 mole) was then added rapidly, followed by a slow addition of 10.8 g of triethylamine. The mixture was stirred at 0° C. for 1 hour, and then was warmed to room temperature and water extracted. The organic solution was then extracted with a saturated sodium bicarbonate solution and water, dried ($MgSO_4$) and concentrated in vacuo. The syrup residue was vacuum distilled to give 15.2 g (60 percent) yield of N-methyl-N-(di-n-butylaminosulfenyl)carbamoyl fluoride, b.p. 84° C./0.15 mm.

Infrared: 5.6μ, C=O; 7.05μ, N—$CH_3$.

NMR: $CDCl_3$; multiplet at δ 0.75 to 1.84 ppm (14H); triplet at δ 3.17 ppm (4H); doublet at δ 3.33 ppm (3H); J=1 Hz.

Anal. Calc'd. for $C_{10}H_{21}FN_2OS$; C, 50.82; H, 8.96; N, 11.85. Found: C, 51.16; H, 8.72; N, 11.86.

EXAMPLE 28

Preparation of S-Methyl
N-[N'-Methyl-N'-(Di-n-butylaminosulfenyl)Carbamoyloxy]-Thioacetimidate A mixture of 4.0 g (0.038 mole) of S-methyl-N-hydroxythioacetimindate, 2.1 g powdered potassium hydroxide, and 0.1 g of dicyclohexyl-18-crown-6 in 200 ml of benzene was stirred 0.5 hr. at room temperature. Then a solution of 9.0 g (0.038 mole) of N-methyl-N-(di-n-butylaminosulfenyl)carbamoyl fluoride in 15 ml of benzene was added dropwise over a 15-minute period. The mixture was stirred at room temperature for 1 hour, water extracted three times, dried ($MgSO_4$), and stripped in vacuo. The ensuing residue was purified by column chromatography on silica gel to give 8.5 g of S-methyl N-N'-methyl-N'-(di-n-butylaminosulfenyl)-carbamoyloxy-thioacetimidate, (69.7 percent yield).

Anal. Calc'd. for $C_{13}H_{27}N_3O_2S_2$: C, 48.56; H, 8.46; N, 13.07. Found: C, 49.36; H, 8.40; N, 13.14.

EXAMPLE 29

Preparation of
S-Ethyl-N-[N'Methyl-N'-(Dimethylaminosulfenyl)carbamoyloxy]thioacetimidate A mixture of 3.3 g powdered potassium hydroxide, 6.0 g (0.05 mole) of 1-(ethylthio)acetaldoximes, and 0.1 g dicyclohexyl-18-crown-6 in benzene was stirred for 1 hr. at 28° C. Then 8.0 g (0.05 mole) of N-methyl-N-(dimethylaminosulfenyl)carbamoyl fluoride was added rapidly with external cooling to hold the temperature at 28°-32° C. The mixture was stirred 2 hrs. at 28° C. and then was extracted three times with water and dried ($MgSO_4$). The benzene was stripped in vacuo, and the residue was recrystallized from diisopropyl ether to give 9.0 g of S-Ethyl N-[N'-methyl-N'-(dimethylaminosulfenyl)carbamoyloxy]thioacetimidate, (72 percent yield), m.p. 46°-48° C.

Anal. Calc'd for $C_8H_{17}N_3O_2S_2$: C, 38.2; H, 6.8; N, 16.7. Found: C, 38.0; H, 6.7; N, 16.7.

EXAMPLE 30

Preparation of
2-Methyl-2-(Methylthio)propionaldehyde
O-[N-Methyl-N-(Dimethylaminosulfenyl)carbamoyl]oxime A mixture of 3.3 g powdered potassium hydroxide, 0.1 g dicyclohexyl-18-crown-6, and 6.7 g (0.05 mole) of 2-methyl-2-(methylthio)propionaldehyde oxime in 200 ml of benzene was stirred 1 hr. at room temperature. N-methyl-N-(dimethylaminosulfenyl)carbamoyl fluoride (8.0 g, 0.05 mole) was then added, and the mixture was stirred overnight at room temperature. The solution was extracted three times with water, dried ($MgSO_4$), and concentrated in vacuo. The oily residue was recrystallized from n-hexane to give 10 g (75.5 percent yield) of 2-methyl-2-(methylthio)propionaldehyde O-[N-methyl-N-(dimethylaminosulfenyl)carbamoyl]oxime, m.p. 48°-50° C.

Anal. Calc'd. for $C_9H_{19}N_3O_2S_2$: C, 40.7; H, 7.2; N, 15.8. Found: C, 40.6; H, 7.0; N, 15.7.

EXAMPLE 31

Preparation of
1-(1'-Carbamoyl-1'-Ethylthio)propionaldehyde
O-[N-Methyl-N-(Dimethylaminosulfenyl)carbamoyl]oxime Dioxane (20 ml), 1.7 g powdered potassium hydroxide, 4.6 g (8.026 mole) of 1-(1'-carbamoyl-1'-ethyl thio)-propionaldehyde oxime, and 0.1 g dicyclohexyl-18-crown-6 were charged to a stirred reaction flask and stirred 2 hrs. at 28° C. Then 4.2 g (0.026 mole) of N-methyl-N-(dimethylaminosulfenyl)carbamoyl fluoride was added rapidly (1 min.). The mixture was stirred overnight at room temperature, and then was poured into one liter of cold water. The aqueous mixture was extracted with methylene chloride, and the methylene chloride extract was then back extracted three times with water and dried ($MgSO_4$). The solvent was evaporated in vacuo, and the residue was recrystallized from ethyl acetate to give 4.0 g (50 percent yield) of 1-(1'-carbamoyl-1'-ethylthio)propionaldehyde 0O-[N-methyl-N-(dimethylaminosulfenyl)carbamoyl]oxime, m.p. 120°-122° C.

Anal. Calc'd for $C_{10}H_{20}N_4OS_2$: C, 38.9; H, 6.5; N, 18.2. Found: C, 38.8; H, 6.4; H, 17.9.

EXAMPLE 32

Preparation of 1-Methylthio-3,3-dimethyl-2-Butanone
O-[N-methyl-N-(Dimethylaminosulfenyl)carbamoyl]oxime A mixture of 2.5 g powdered potassium hydroxide, 0.1 g. of dicyclohexyl-18-crown-6, and 6.0 g (0.037 mole) of 1-methylthio-3,3-dimethyl-2-butanone oxime in 200 ml of benzene was stirred 2 hrs. at 28° C. Then 5.9 g (0.037 mole) of N-methyl-N-(dimethylaminosulfenyl)-carbamoyl fluoride was added rapidly. The mixture was stirred 20 hrs. at room temperature, water washed three times, dried ($MgSO_4$), and the benzene solvent was removed in vacuo. The product, 1-methylthio-3,3-dimethyl-2-butanone O-[N-methyl-N-(dimethylaminosulfenyl)carbamoyl]oxime, was obtained as a heavy syrup which would not crystallize, 8 g. (73.7 percent yield).

Anal. Calc'd. for $C_{11}H_{23}N_3O_2S_2$: C, 45.0; H, 7.9; N, 14.3. Found: C, 45.4; H, 7.6; N, 13.9.

EXAMPLE 33

Preparation of S-Methyl N-[N'-Methyl-N'-(Diisopropylaminosulfenyl)carbamoyloxy]thioacetimidate Powdered potassium hydroxide (2.5 g), 4.7 g. 10.045 mole) of S-methyl-N-hydroxythioacetimidate, 0.11 g dicyclohexyl-18-crown-6, and benzene (200 mol) were combined and stirred 0.5 hr. at room temperature. Then 9.4 g (0.045 mole) of N-methyl-N-(diisopropylaminosulfenyl)carbamoyl fluoride were added. The mixure was stirred at room temperature for 1 hr., and then was water washed four times, dried ($MgSO_4$), and the benzene solvent was removed under vacuum. The residue was recrystallized from diisopropyl ether to give 9 g (67.3 percent yield) of S-methyl N-[N'-methyl-N'-(diisopropylaminosulfenyl)carbamoyloxy]thioacetimidate, m.p. 79°-80° C.

Anal. Calc'd. for $C_{11}H_{23}N_3O_2S_2$: C, 45.02; H, 7.90; N, 14.32. Found: C, 45.10; H, 7.59; N, 14.32.

EXAMPLE 34

Preparation of N-Methyl-N-(4-Morpholino-sulfenyl)Carbamoyl Fluoride

Sulfur dichloride (61.8 g, 0.6 mole) was charged to a 2-liter reaction flask containing 700 ml of methylene chloride at −15° C. A mixture of 52.7 g (0.6 mole) of morpholine and 60.6 g (0.6 mole) of triethylamine was then added dropwise with stirring over a 1.5-hour period. The reaction was held at −10° C. during the addition. After the addition was completed, the mixture was stirred at −10° to −15° C. for 0.5 hour, and then was used in a reaction (below) with methylcarbamoyl fluoride without filtration of the precipitated amine salts.

While the above reaction was in progress, 700 ml of methylene chloride was charged to a polyethylene reactor and cooled to −15° C. The reactor was equipped with a stainless steel thermocouple well and stirrer, and a Teflon addition tube fitted to a dropping funnel and nitrogen inlet line. A dry-ice tray was fitted around the Teflon tube so as to act as a cold finger condenser. Liquid hydrogen fluoride (11 g, 0.55 mole) was weighed out into a tared cold trap, and then was poured rapidly into the reactor. Methyl isocyanate (31.4 g, 0.55 mole) was then added dropwise while the temperature was maintained at −10° C. The mixture of 4-morpholinosulfenyl chloride and triethylamine hydrochloride prepared above was then added to the reactor rapidly by pouring it in through the Teflon sidearm. The mixture was stirred and 55.7 g of triethylamine was added over a 30-minute period. The mixture was then warmed to +10° C. and was extracted with water and then sodium bicarbonate solution. The methylene chloride solution was dried with $MgSO_4$, and was concentrated in vacuo to give a brown oil which solidified when triturated with n-hexane. The solids were collected by filtration and dried in vacuo to give 75 g (64 percent yield) of crude N-methyl-N-(4-morpholino-sulfenyl)carbamoyl fluoride.

EXAMPLE 35

Preparation of S-Methyl-N-[N'-Methyl-N'-(4-Morpholinosulfenyl)carbamoyloxy]-Thioacetimidate This example illustrates the use of a phase transfer catalyst in the carbamoylation of an oxime compound. To a solution of 291 g (1.5 m.) of N-Methyl-N-(4-morpholinothio)carbamoyl fluoride in 8500 ml of benzene were added at room temperature 158 g (1.5 m) of 1-methylthioacetaldoxime and 22.8 g (0.045 m) of tricaprylyl methyl ammonium chloride (av. mol. wt. about 507). A 126.4 g (1.58 eq) quantity of 50% aqueous sodium hydroxide solution was added at 20°-22° C. over a 50 min. period. The mixture was then stirred for 3 hours. The benzene solution was washed with water until the washings became neutral, and then concentrated at 33° C. (120 mm Hg) until the solution just turned cloudy. Upon cooling to 8°-9° C., white crystalline solid was collected. After filtration, the solution was concentrated further yielding a second crop of product. The total yield of the product (m.p. 129° to 130° C.) in two crops was 80.6% (337.6 g).

Analysis: Cal'd for $C_9H_{17}N_3O_3S_2 = $ C,38.69; H,6.13; N,15.04. Found=C,38.37; H,6.35; N,14.79.

The following compositions can be prepared by the procedures set forth in the above examples and in the methods described above and are illustrative of the new compounds of this invention:

S-methyl-N-[N'-methyl-N'-(4-morpholinosulfenyl)carbamoyloxy]thioacetimidate

S-ethyl-N-[N'-methyl-N'-(4-morpholinosulfenyl)carbamoyloxy]thioacetimidate

S-isopropyl-n'[N'-methyl-N'-(4-morpholinosulfenyl)carbamoyloxy)thioacetimidate

S-(2-cyanoethyl)-N-[N'-methyl-N'-(4-morpholinosulfenyl)carbamoyloxy]thioacetimidate S-(1-butyl)-N-[N'-methyl-N'-(4-morpholinosulfenyl)carboxyloxy]thioacetimidate S-phenyl-N-[N'-methyl-N'-(4-morpholinosulfenyl)carbamoyloxy]thioacetimidate S-(aminocarbonylmethylene)-N-[N'-methyl-N'-(4-morpholinosulfenyl)carbamoyloxy]thioacetimidate S-methyl-N-[N'-methyl-N'-(4-morpholinosulfenyl)carbamoyloxy]thiopropionimidate S-methyl-N-[N'-ethyl-N'-(4-morpholinosulfenyl)carbamoyloxy]thioacetimidate S-methyl-N-[N'-isopropyl-N'-(4-morpholinosulfenyl)carbamoyloxy]thioacetimidate S-methyl-N-[N'-phenyl-N'-(4-morpholinosulfenyl)carbamoyloxy]thioacetimidate S-methyl-N-[N'-(3-chlorophenyl)-N'-(4-morpholinesulfenyl)carbamoyloxy]thioacetimidate S-methyl-N-[N'-methyl-N'-(4-methyl-1-piperazinosulfenyl)carbamoyloxy]thioacetimidate S-methyl-N-[N'-methyl-N'-(3-tetrahydro-1,3-oxazinosulfenyl)carbamoyloxy]thioacetimidate S-methyl-N'[N'-methyl-N'-(4-thiomorpholinosulfenyl)carbamoyloxy]thioacetimidate S-methyl-N-[N'-methyl-N'-(dimethylaminosulfenyl)carbamoyloxy]thioacetimidate S-methyl-N-[N'-methyl-N'-(methylethylaminosulfenyl)carbamoyloxy]thioacetimidate S-methyl-N-[N'-methyl-N'-(methylphenylaminosulfenyl)carbamoyloxy]thioacetimidate S-methyl-N-[N'-methyl-N'-(methylbenzylaminosulfenyl)carbamoyloxy]thioacetimidate S-methyl-N-[N'-methyl-N'-(ethylcyclohexylaminosulfenyl)carbamoyloxy]thioacetimidate
S-methyl-N-[N'-methyl-N'-(methoxymethylaminosulfenyl)carbamoyloxy]thioacetimidate
O-ethyl-N-[N'-methyl-N'-(4-morpholinosulfenyl)carbamoyloxy]acetimidate
2-Methyl-2-(methylthio)propionaldehyde O-[N-methyl-N-(4-morpholinosulfenyl)carbamoyl]oxime
2-methyl-2-(methylsulfonyl)propionaldehyde O-[N-methyl-N-(4-morpholinosulfenyl)carbamoyl]oxime
2-cyano-2-methylpropionaldehyde O-[N-methyl-N-(4-morpholinosulfenyl)carbamoyl]oxime
5-methyl-4-N-[N'-methyl-N'-(4-morpholinosulfenyl)-carbamoyloxy]imino-1,3-oxathiolane
2-N-[N'-methyl-N'-(4-morpholinosulfenyl)carbamoyloxy]imino-1,4-oxathiane
2-N-[N'-methyl-N'-(4-morpholinosulfenyl)carbamoyloxy]imino-1,4-dithiane
3,3-Dimethyl-2-N-[N'-methyl-N'-(4-morpholinosulfenyl)carbamoyloxy]imino-5-oxo-perhydro-1,4-thiazine
5,5-Dimethyl-4-N-[N'-methyl-N'-(4-morpholinosulfenyl)carbamoyloxy]imino-1,3-dithiolane
2-N-[N'-methyl-N'-(4-morpholinosulfenyl)carbamoyloxy]imino-3,5,5-trimethyl-1,3-thiazolidine-4-one
S-Methyl-N-[N'-Methyl-N'-(3,3-Dimethyl-4-Morpholinosulfenyl)carbamoyloxy]thioacetimidate
2-methyl-2-nitropropionaldehyde O-[N-methyl-N-(4-morpholinosulfenyl)carbamoyl]oxime
N-methyl-N-(4-morpholinosulfenyl) 3-isopropylphenyl carbamate
N-methyl-N-(4-morpholinosulfenyl) 3-sec-butylphenyl carbamate
N-methyl-N-(4-morpholinosulfenyl) 2-isopropoxyphenyl carbamate
N-methyl-N-(4-morpholinosulfenyl) 4-dimethylamino-3,5-xylyl carbamate
N-methyl-N-(4-morpholinosulfenyl) 4-dipropylamino-3,5-xylyl carbamate
N-methyl-N-(4-morpholinosulfenyl) 4-methylthio-3,5-xylyl carbamate
N-methyl-N-(4-morpholinosulfenyl) 4-methylthio-3-tolyl carbamate
N-methyl-N-(4-morpholinosulfenyl) 2,3-dihydro-2,2-dimethyl-7-benzofuranyl carbamate
N-methyl-N-(diisopropylaminosulfenyl) 2,3-dihydro-2,2-dimethyl-7-benzofuranyl carbamate
N-methyl-N-(dimethylaminosulfenyl) 2,3-dihydro-2,2-dimethyl-7-benzofuranyl carbamate
N-methyl-N-(4-morpholinosulfenyl) 3-dimethylaminomethyleneaminophenyl carbamate
N-methyl-N-(4-morpholinosulfenyl) 2-dimethylcarbamoyl-3-methyl-5-pyrazolyl carbamate
N-methyl-N-(4-morpholinosulfenyl) 3-isopropyl-5-methylphenyl carbamate
N-methyl-N-(4-morpholinesulfenyl) 4-methoxy-3,5-xylyl carbamate
N-methyl-N-(4-morpholinosulfenyl) 2-methoxy-4-methylphenyl carbamate
N-methyl-N-(4-morpholinosulfenyl) 2-chloro-4-methylphenyl carbamate
N-methyl-N-(di-n-butylaminosulfenyl) 3-sec-amylphenyl carbamate
N-methyl-N-(4-morpholinosulfenyl) 5,6-dimethyl-5,6,7,8-tetrahydro 1-naphthyl-carbamate
2-N-[N'-methyl-N'-(4-morpholinosulfenyl)carbamoyloxy]imino-1,3-dithiolane
Propiophenone O-[N-methyl-N-(4-morpholinosulfenyl)carbamoyl]oxime
O-[N-methyl-N-(4-morpholinosulfenyl)carbamoyl]-phenylglyoxylonitrileoxime
1-chloro-1-(ethylthio)formaldehyde O-[N-methyl-N-(4-morpholinosulfenyl)carbamoyl]oxime
1,1-bis(ethylthio)formaldehyde O-[N-methyl-N-(4-morpholinosulfenyl)carbamoyl]oxime
S-[2-(N-methylcarbamoyloxy)ethyl]-N-[N'-methyl-N'-(4-morpholinosulfenyl)carbamoyloxy]thiopropionimidate
S-Methyl-1-dimethylcarbamoyl-N-[N'-methyl-N'-(4-morpholinosulfenyl)carbamoyloxy]thioformimidate
O-Methyl-1-dimethylcarbamoyl-N-[N'-methyl-N'-(4-morpholinosulfenyl)carbamoyloxy]formimidate
3,3-dimethyl-1-(methylthio)-2-butanone O-[N-methyl-N-(4-morpholinosulfenyl)carbamoyl]oxime
α-(methylcarbamoyloxy)acetophenone O-[N-methyl-N-(4-morpholinesulfenyl)carbamoyl]oxime
Methyl 2-Methylpropenyl ketone O-[N-methyl-N-(4-morpholinesulfenyl)carbamoyl]oxime
α-(methylsulfinyl)acetophenon O-[N-methyl-N-(4-morpholinosulfenyl)carbamoyl]oxime
exo-3-chloro-endo-6-cyano-2-norbornanone O-[N-methyl-N-(4-morpholinosulfenyl)carbamoyl]oxime
S-isopropyl-1-acetyl-N-[N'-methyl-N'-(4-morpholinosulfenyl)carbamoyloxy]thioformimidate
5,5-dimethyl-1,4-dithia-6-N-[N'-methyl-N'-(4-morpholinosulfenyl)carbamoyloxy]-iminocycloheptane
2,4-dimethyl-1,3-dithiolane-2-carboxaldehyde O-[N-methyl-N-(4-morpholinosulfenyl)carbamoyl]oxime
Isopropyl 5-(methylthio)-2-thienyl ketone O-[N-methyl N-(4-morpholinosulfenyl)carbamoyl]oxime
2,2-dimethyl-3-hydroxypropionaldehyde O-[N-methyl-N-(4-morpholinosulfenyl)carbamoyl]oxime
2,2-dimethyl-3-(methylsulfonyloxy)propionaldehyde O-[N-methyl-N-(4-morpholinosulfenyl)carbamoyl]oxime
3,3-dimethyl-4-N-[N-methyl-N-(4-morpholinosulfenyl)-carbamolyoxy]imino-tetrahydrothiophene
S-methyl-N-[N'-methoxymethyl-N'-(4-morpholinosulfenyl)carbamoyloxy]thioacetimidate
S-methyl N-[N'-allyl-N'-(4-morpholinosulfenyl)carbamoyloxy]thioacetimidate
S-methyl N-[N'-(2-chloroethyl)-N'-(4-morpholinosulfenyl)carbamoyloxy]thioacetimidate
S-methyl-N-[N'-cyanomethyl-N'-(4-morpholinosulfenyl)carbamoyloxy]thioacetimidate
S-methyl N-[N'-benzyl-N'-(4-morpholinosulfenyl)carbamoyloxy]thioacetimidate
S-methyl N-[N'-methoxy-N'-(4-morpholinosulfenyl)-carbamoyloxy]thioacetimidate
S-methyl N-[N'-(2-furylmethyl)-N'-(4-morpholinosulfenyl)carbamoyloxy]thioacetimidate
S-methyl N-[N'-(1-acetyl-3-piperidylmethyl)-N'-(4-morpholinosulfenyl)carbamoyloxy]thioacetimidate
S-methyl N-[N'-(3-tetrahydrothiophenylmethyl)-N'-(4-morpholinosulfenyl)carbamoyloxy]thioacetimidate
S-methyl N-[N'-cyclohexyl-N'-(4-morpholinosulfenyl)-carbamoyloxy]thioacetimidate
S-methyl N-[N'-(4-nitrophenyl)-N'-(4-morpholinosulfenyl)carbamoyloxy]thioacetimidate
S-methyl N-[N'-(4-methoxyphenyl)-N'-(4-morpholinosulfenyl)carbamoyloxy]thioacetimidate
S-methyl N-[N'-(2-chloro-4-methylphenyl)-N'-(4-morpholinosulfenyl)carbamoyloxy]thioacetimidate Certain representative examples of the new compounds were evaluated to determine their pesticidal activity against mites and certain insects, including an aphid, caterpillar, a beetle and a fly. The new compounds were also tested for phytotoxicity on important economic crops including bean, soybean, corn, tomato and cotton. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (Aphis fabae Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 250 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Bait Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 250 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (Epilachna varivestis, Muls.), reared on Tendergreen bean plants at a temperature of 80°±5° F. and 50±5 percent relative humidity, were the test insects.

The test compounds were formulated by diluting the stock suspension with water to give a suspension containing 250 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 250 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 pecent. Flies which showed no sign of movement on prodding were considered dead.

Mite Foliage Spray Test

Adults and nymphal stage of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 250 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The spayed plants were held at 80±5 percent relative humidity for six days, after which a mortality count of motile forms was made. Microscopic examination for motile forms was made on the leaves of the test plants. Any individual which was capable of locomotion upon prodding was considered living.

Phytotoxicity Test

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

Mammalian Toxicity

These compositions were also evaluated to determine their peroral toxicity to mammals by conventional methods. The animal selected for this experiment was the rat. The test results obtained are expressed in terms of the number of milligrams of composition per kilogram of weight of the animal required to achieve a mortality rate of 50 percent ($LD_{50}$).

The results of these experiments are summarized and set forth in Table I, below.

TABLE I

BIOLOGICAL PROPERTIES OF REPRESENTATIVE N-AMINOSULFENYL CARBAMATES

| Compound Number* | Insect Toxicity, % Kill at 250 ppm** | | | | | RAT Acute Oral $LD_{50}$ mg/kg | Crop Phytotoxicity, Injury Rating at 2500 ppm*** | | | | |
|---|---|---|---|---|---|---|---|---|---|---|---|
| | BA | TSM | SAW | MBB | HF | | GB | CN | TOM | COT. | SOYBN. |
| 3 | 100 | 50 | 100 | 100 | 100 | 200 | 1 | 1 | 1 | 1 | 1 |
| 4 | 100 | 100 | 100 | 100 | 100 | 141 | 1 | 1 | 1 | 1 | 2 |
| 5 | 100 | 100 | 100 | 100 | 100 | 19.8 | 1 | 1 | 1 | 1 | 1 |
| 6 | 100 | 100 | 10 | 0 | 100 | 1.2 | 1 | 1 | 1 | 1 | 1 |
| 7 | 100 | 100 | 100 | 100 | 100 | 28.1 | 2 | 1 | 1 | 1 | 1 |
| 8 | 100 | 100 | 100 | 100 | 100 | 22 | 1 | 1 | 1 | 1 | 1 |
| 9 | 100 | 100 | 100 | 100 | 100 | 16 | 1 | 1 | 2 | 1 | 2 |
| 10 | 100 | 100 | 100 | 100 | 100 | — | 1 | 1 | 1 | 3 | 1 |
| 11 | 100 | 50 | 100 | 100 | 100 | 141 | 1 | 1 | 2 | 1 | 1 |
| 12 | 100 | 100 | 100 | 100 | 100 | 141 | 1 | 1 | 1 | 1 | 1 |
| 14 | 100 | 0 | 0 | 0 | 0 | — | 1 | 1 | 1 | 1 | 1 |
| 16 | 100 | 100 | 100 | 100 | 100 | — | 1 | 1 | 1 | 1 | 1 |
| 17 | 100 | 80 | 100 | 100 | 100 | 178 | 2 | 2 | 1 | 2 | 2 |
| 23 | 100 | 100 | 100 | 100 | 100 | 15 | 1 | 1 | 1 | 2 | 1 |
| 24 | 100 | 100 | 100 | 100 | 100 | 28.3 | 2 | 1 | 2 | 2 | 3 |
| 28 | 100 | 50 | 100 | 100 | 100 | 317 | 1 | 1 | 1 | 1 | 1 |

*Compound Number corresponds to specific Examples above.
**BA = bean aphid, TSM = two spotted mite, SAW = southern armyworm, MBB = Mexican bean bettle, HF = housefly
***GB = green beans, CN = corn, TOM = tomato, SOYBN = soybeans, COT = cotton At higher dosage rates than those indicated in Table I, all of the compositions of this invention may be expected to exhibit some activity against the various test species, however, the data presented in Table I above clearly indicates a high degree of selectivity for some compositions and excellent broad spectrum activity for others. It will be understood that the insect species employed in the above tests are merely representative of a wide variety of pests that can be controlled by the use of the novel compounds of this invention. The extremely low mammalian toxicity of compounds 3, 4, 11, 12, 17 and 28 is particularly noteworthy due to the critical importance of safety to warm blooded creatures in assessing the practical utility of agricultural pesticides.

While mammalian and insect toxicity are obvious critical factors in determining the ultimate utility of agricultural insecticides, the toxicity of the pesticide to crop plants where insect infestations are found is equally important. The extremely low phytotoxicity of the compounds tested toward important economic crops is particularly noteworthy in view of the very high order of insect toxicity possessed by these compounds. This is a highly significant characteristic and one that profoundly influences the ultimate utility of the novel compounds of this invention as agricultural pesticides.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. A compound of the formula:

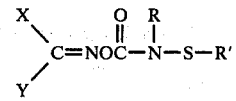

wherein:
R is hydrogen, lower alkyl, lower alkenyl, lower alkoxy, or lower cycloalkyl, either unsubstituted or, except where R is hydrogen, substituted with one or more chloro, bromo, fluoro, nitro or cyano substituents, or a combination thereof, or phenyl or lower phenylalkyl, either unsubstituted or substituted with one or more chloro, bromo, fluoro, nitro, cyano, lower alkyl, lower haloalkyl or lower alkoxy substituents or a combination thereof;
R' is lower dialkylamino or morpholino which may be unsubstituted or aliphatically substituted with one or more chloro, fluoro, bromo, nitro, lower haloalkyl or lower alkoxy;
X is alkylthio, cyanoalkyl, cyanoalkylthio;
Y is hydrogen or alkyl;
with the proviso that the total number of aliphatic carbon atoms in X and Y shall not exceed 12.

2. A compound according to claim 1 wherein R' is unsubstituted morpholino or lower dialkylamino.

3. A compound according to claim 2 wherein
X is alkylthio;
Y is alkyl.

4. A compound of the formula:

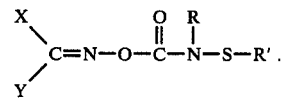

wherein:
R is hydrogen, lower alkyl, lower alkoxy, lower alkenyl or lower cycloalkyl which may be unsubstituted or, except in the case of hydrogen, substituted with one or more bromo, chloro, fluoro, or nitro substituents or a combination thereof;
R' is morpholino, which may be unsubstituted or substituted with one or more chloro, bromo, fluoro, nitro, lower alkyl, lower haloalkyl or lower alkoxy substituents or a combination thereof;
X is alkylthio; and
Y is hydrogen, alkyl or alkenyl; with the proviso that the total number of carbon atoms in X and Y shall not exceed about 12.

5. A compound according to claim 4 wherein X is methyl and Y is methylthio.

6. A compound according to claim 4 wherein R is lower alkyl.

7. A compound according to claim 4 wherein R is methyl.

8. A compound according to claim 5 wherein R is methyl.

9. A compound of the formula:

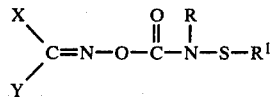

wherein:
R is hydrogen or lower alkyl;

R¹ is lower dialkylamino or morpholino;

X is alkylthio;

Y is hydrogen or alkyl, with the proviso that the total number of carbon atoms in each of said alkyl does not exceed twelve.

10. S-(2-Cyanoethyl)-N-[N'-methyl-(4-morpholinosulfenyl)carbamoyloxy]thioacetimidate.

11. S-Methyl-N-[N'-methyl-N'-(dimethylaminosulfenyl)carbamoyloxy]thioacetimidate.

12. S-methyl N-[N'-methyl-N'-(diisopropylaminosulfenyl)carbamoyloxy]thioacetimidate.

13. S-methyl-N-[N'-methyl-N'-(di-n-butylaminosulfenyl)carbamoyloxy]-thioacetimidate.

14. S-methyl N-[N'-methyl-N'-(4-morpholinosulfenyl)carbamoyloxy]-thioacetimidate.

15. A pesticide composition comprising an acceptable carrier and as the active toxicant an insecticidally, miticidally or nematocidally effective amount of a compound according to claim 1.

16. A pesticide composition comprising an acceptable carrier and as the active toxicant an insecticidally, miticidally or nematocidally effective amount of a compound according to claim 2.

17. A pesticide composition comprising an acceptable carrier and as the active toxicant an insecticidally, miticidally or nematocidally effective amount of a compound according to claim 3.

18. A pesticide composition comprising an acceptable carrier and an insecticidally, miticidally or nematicidally effective amount of a compound of the formula:

$$\begin{array}{c}X\\ \phantom{X}\diagdown\\ \phantom{XXX}C=N-O-\overset{O}{\underset{\|}{C}}-N-S-R'\\ \phantom{X}\diagup\phantom{XXXXXXXXXXX}\diagdown\\ Y\phantom{XXXXXXXXXXXXXXXX}R\end{array}$$

wherein:

R is hydrogen, lower alkyl, lower alkoxy, lower alkenyl or lower cycloalkyl which may be unsubstituted or, except in the case of hydrogen substituted with one or more bromo, chloro, fluoro, or nitro substituents or a combination thereof;

R' is morpholino, which may be unsubstituted or substituted with one or more chloro, bromo, fluoro, nitro, lower alkyl, lower haloalkyl or lower alkoxy substituents or a combination thereof;

X is alkylthio; and

Y is hydrogen, alkyl or alkenyl; with the proviso that the total number of carbon atoms in X and Y shall not exceed about 12.

19. A composition according to claim 18 wherein X is methyl and Y is methylthio.

20. A composition according to claim 18 wherein R is lower alkyl.

21. A composition according to claim 18 wherein R is methyl.

22. A composition according to claim 19 wherein R is methyl.

23. A pesticide composition comprising an acceptable carrier and an insecticidally, miticidally or nematicidally effective amount of a compound of claim 9.

24. A pesticide composition comprising an acceptable carrier and as the active toxicant an insecticidally, miticidally or nematocidally effective amount of a compound according to claim 14.

25. A composition according to claim 15 wherein said compound is S-methyl N-[N'-methyl-N'-(diisopropylaminosulfenyl)carbamoyloxy]-thioacetimidate.

26. A composition according to claim 15 wherein said compound is S-methyl N-[N'-methyl-N'-(di-n-butylaminosulfenyl)carbamoyloxy]-thioacetimidate.

27. A composition according to claim 18 wherein said compound is S-methyl N-[N'-methyl-N'-(4-morpholinosulfenyl)carbamoyloxy]-thioacetimidate.

28. A method of controlling insects, mites and nematodes which comprises subjecting them to an insecticidally, miticidally or nematocidally effective amount of a compound according to claim 1.

29. A method of controlling insects, mites and nematodes which comprises subjecting them to an insectcidally, miticidally or nematocidally effective amount of a compound according to claim 2.

30. A method of controlling insects, mites and nematodes which comprises subjecting them to an insecticidally, miticidally or nematocidally effective amount of a compound according to claim 3.

31. A method of controlling pests which comprises subjecting them to an insecticidal, miticidal or nematocidal amount of a compound of the formula:

$$\begin{array}{c}X\\ \phantom{X}\diagdown\\ \phantom{XXX}C=N-O-\overset{O}{\underset{\|}{C}}-N-S-R'\\ \phantom{X}\diagup\phantom{XXXXXXXXXXX}\diagdown\\ Y\phantom{XXXXXXXXXXXXXXXX}R\end{array}$$

wherein:

R is hydrogen, lower alkyl, lower alkoxy, lower alkenyl or lower cycloalkyl which may be unsubstituted or, except in the case of hydrogen, substituted with one or more bromo, chloro, fluoro or nitro substituents or a combination thereof;

R' is morpholino, which may be unsubstituted or substituted with one or more chloro, bromo, fluoro, nitro, lower alkyl, lower haloalkyl or lower alkoxy substituents or a combination thereof;

X is alkylthio; and

Y is hydrogen, alkyl or alkenyl; with the proviso that the total number of carbon atoms in X and Y shall not exceed about 12.

32. A method of controlling pests which comprises subjecting them to an insecticidal, miticidal or nematicidal amount of a compound of claim 9.

33. A method of controlling insects, mites and nematodes which comprises subjecting them to an insecticidally, miticidally or nematocidally effective amount of a compound according to claim 14.

34. A method according to claim 31 wherein X is methyl and Y is methylthio.

35. A method according to claim 31 wherein R is lower alkyl.

36. A method according to claim 31 wherein R is methyl.

37. A method according to claim 28 wherein said compound is S-methyl N-[N'-methyl-N'-(diisopropylaminosulfenyl)carbamoyloxy]thioacetimidate.

38. A method according to claim 28 wherein said compound is S-methyl N-[N'-methyl-N'-(di-n-butylaminosulfenyl)carbamoyloxy]-thioacetimidate.

39. A method according to claim 31 wherein said compound is S-methyl N-[N'-methyl-N'-(4-morpholinosulfenyl)carbamoyloxy]-thioacetimidate.

* * * * *